United States Patent [19]

Rüdiger et al.

[11] Patent Number: 4,887,611

[45] Date of Patent: Dec. 19, 1989

[54] PLASTER FOR CONDUCTING SKIN PATCH TESTS

[75] Inventors: Günther Rüdiger, Reinbek; Ulf Peters, Büchen, both of Fed. Rep. of Germany

[73] Assignee: Merck Patent Gesellschaft Mit Beschränkter Haftung, Darmstadt, Fed. Rep. of Germany

[21] Appl. No.: 151,768

[22] Filed: Feb. 3, 1988

Related U.S. Application Data

[63] Continuation-in-part of Ser. No. 892,172, Aug. 1, 1986, abandoned.

[30] Foreign Application Priority Data

Aug. 3, 1985 [DE] Fed. Rep. of Germany ....... 3527893

[51] Int. Cl.$^4$ .............................................. A61B 15/00
[52] U.S. Cl. ................................... 128/743; 604/304; 604/307
[58] Field of Search ................ 128/743, 744; 604/289, 604/304, 306, 307, 890, 892, 896, 897

[56] References Cited

U.S. PATENT DOCUMENTS

| | | | |
|---|---|---|---|
| 2,235,436 | 3/1941 | Laub | 128/743 |
| 2,304,817 | 12/1942 | Grozin | 128/743 |
| 3,212,495 | 10/1965 | Osbourn et al. | 128/743 |
| 3,894,531 | 7/1975 | Saunders, Jr. | 128/743 |
| 4,214,592 | 7/1980 | Jacquet et al. | 128/743 |
| 4,390,027 | 6/1983 | Alani et al. | 128/743 |
| 4,450,844 | 5/1984 | Quisno | 128/743 |
| 4,666,441 | 5/1987 | Andriola et al. | 604/304 |
| 4,695,277 | 9/1987 | Lauk | 604/304 |

OTHER PUBLICATIONS

Pirila et al., The Chamber Test, 1966.

*Primary Examiner*—Max Hindenburg
*Assistant Examiner*—J. P. Lacyk

[57] ABSTRACT

The invention relates to a new plaster package which contains a plaster ready for use for skin patch tests. The plaster package has occlusion chambers which contain test allergens, each in semiliquid vehicles with doses of defined volume.

12 Claims, 2 Drawing Sheets

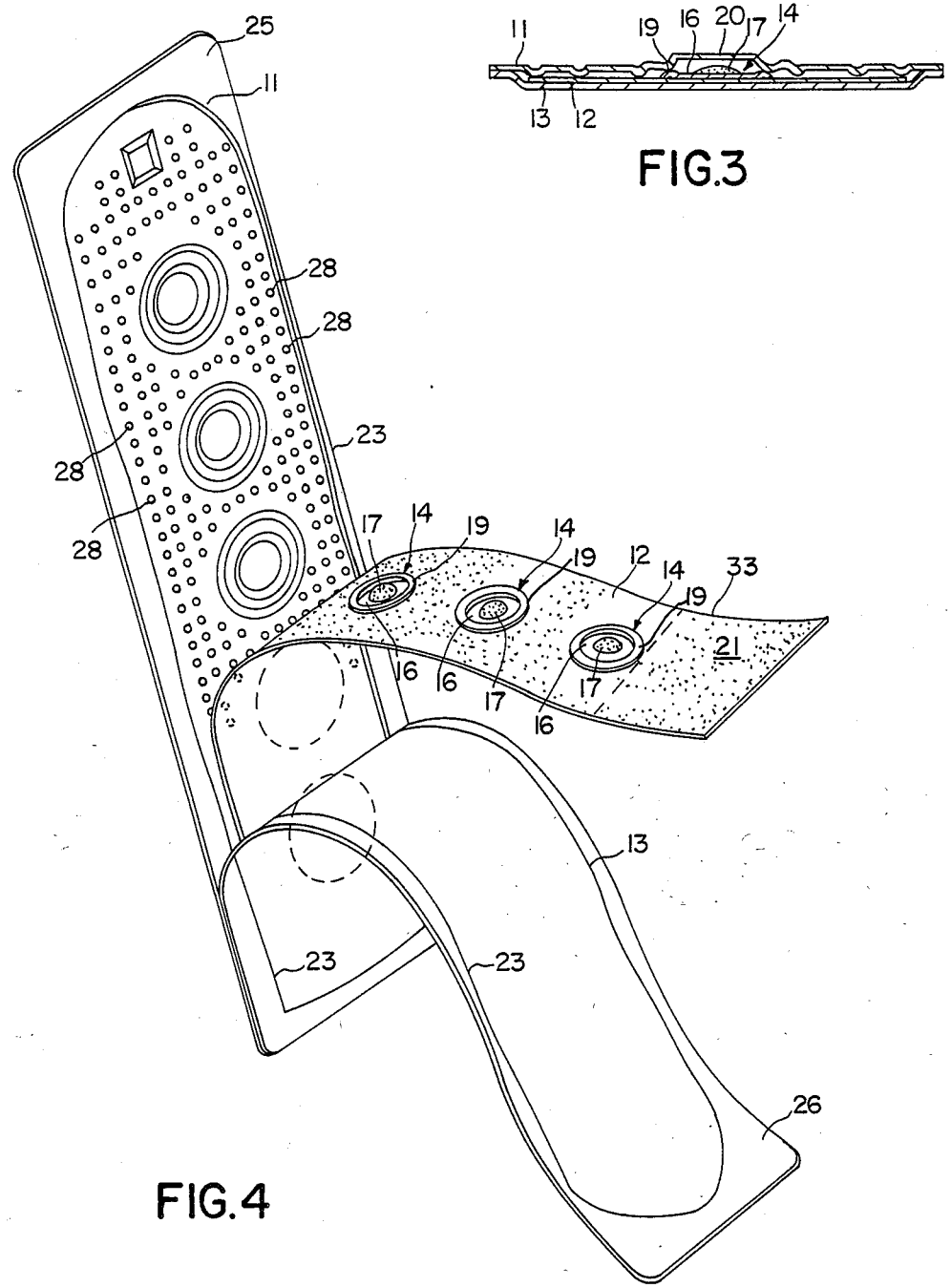

PLASTER FOR CONDUCTING SKIN PATCH TESTS

CROSS-REFERENCE TO RELATED APPLICATION

This application is a continuation-in-part of application Ser. No. 892,172, filed Aug. 1, 1986 abandoned.

BACKGROUND OF THE INVENTION

(1) Field of the Invention

The invention relates to a plaster which is ready for use for skin patch tests, has occlusion chambers and contains test allergens. Each test allergen is in a semiliquid vehicle with doses of defined volume in the occlusion chambers and is enveloped in a protective pack. This test plaster can be used for the detection of allergic reactions in the diagnosis of allergies.

(2) Prior Art

Plasters which have occlusion chambers for skin patch tests are known. A particularly distinguished position in the field is occupied in the present-day patch testing by the Finn Chamber Test of V. Pirilä (compare H.-J. Bandmann and S. Fregert, Epicutan-Testung (Patch testing) published by Springer, Berlin Heidelberg New York, 1982, page 43; German Offenlegungsschrift No. 2,420,345) in which, before the actual test, the test substances are introduced manually into occlusion chambers which are made of aluminum.

It is important that the quantity of allergen introduced into these chambers be extremely accurate (compare T. Fischer and H. Maibach, Contact Dermatitis 11 (3), pages 137-140 (1984). This is because there may be false-positive or false-negative results in the test if the amounts introduced are not uniform, despite the test substances being standardized and manufactured industrially. This fact can crucially effect and impair the validity of patch tests. Moreover, if too much test substance is introduced into a chamber, the test plaster may become detached from the patient's skin.

In particular, under the conditions of routine procedure in a medical practice, it is frequently impossible to measure the amounts of allergen introduced into the chambers with sufficient accuracy. Moreover, accurate application of customary test ointments from small vials or syringes demands considerable time, experience and patience.

OBJECT OF THE INVENTION

The invention has the object of providing those skilled in the art, in particular the practicing physician carrying out the test, with a test plaster which includes the modern chamber technique and already contains the test allergens in accurately defined amounts so that the kit is immediately ready for use, without the expenditure of additional effort, and in which, once the protective pack has been removed, the plaster can be directly applied to the patient, as a rule onto the patient's back.

The object is achieved by the plaster for patch skin tests according to the invention.

Upon further study of the specification and appended claims, further objects and advantages of this invention will become apparent to those skilled in the art.

SUMMARY OF THE INVENTION

The instant invention contemplates intoducing doses of defined volume of test allergens, each in semiliquid vehicles, into occlusion chambers, and then enveloping the resulting plaster in a protective pack.

It is preferable to use the known "FINN CHAMBERS", in particular the "FINN CHAMBERS ON SCANPOR" (FCS) (compare loc. cit.) in which aluminum chambers are preferably lined with a thin film of inert plastic, for example composed of polytetrafluoroethylene, polypropylene or polyethylene—which prevents reaction of the aluminum chambers with certain test substances, for example mercury-and in which mixtures containing test substances and semiliquid vehicles are mechanically introduced into the chambers.

Suitable semiliquid vehicles are customary bases for creams, ointments or pastes; petroleum Jelly sold under the trademark "VASELINE" is preferred, but adeps lanae and oily cream, for example, are also very suitable.

BRIEF DESCRIPTION OF THE DRAWINGS

Various other objects, features and attendant advantages of the present invention will become more fully appreciated as the same becomes better understood when considered in conjunction with the accompanying drawings, in which like reference characters designate the same or similar parts throughout the several views, and wherein:

FIG. 3 is an elevation taken along line 3—3 of FIG. 1, and FIG. 4 is a perspective view showing the three sections or layers of the plaster package being delaminated.

DESCRIPTION OF THE PREFERRED EMBODIMENT

Figure 1:
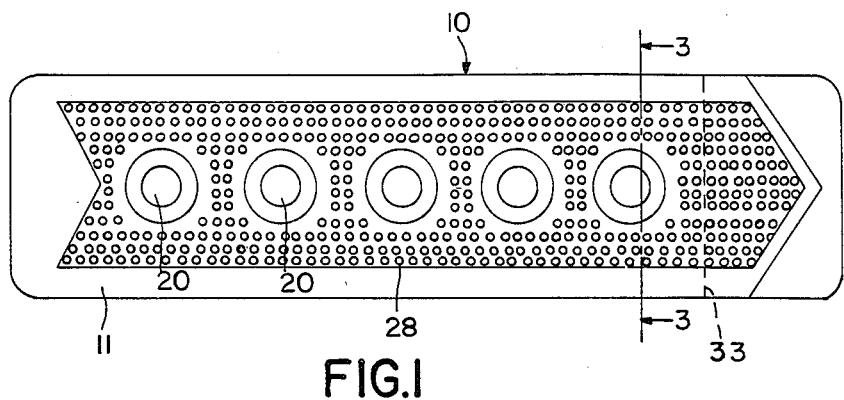
FIG. 1 is a top view of a plaster package in accordance with the instant invention.
Figure 2:
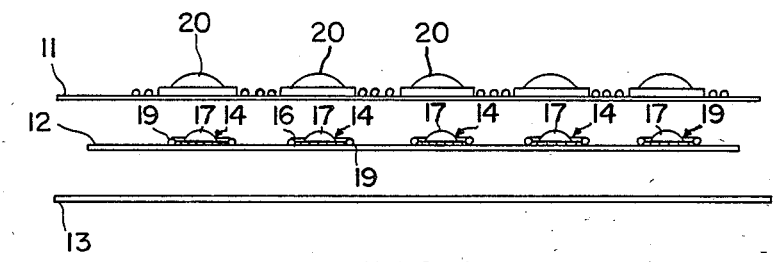
FIG. 2 is a side view of a plaster package configured in accordance with the principles of the instant invention shown exploded into three sections, i.e., an upper foil, an FCS plaster and a lower foil.

In accordance with the principles of the instant invention, doses of defined volumes of test allergens are introduced in semi-liquid vehicles into inclusion chambers and then enveloped by a protective pack. It is preferable to use the known "FINN CHAMBERS", in particular the "FINN CHAMBERS ON SCANPOR" (FCS) in which aluminum chambers are preferably lined with a thin film of inert plastic. The plastic may be polytetrafluoroethylene, polypropylene or polyethylene and prevents reaction of the aluminum chambers with the case of substances which, for example, include mercury. In accordance with the instant invention, the mixtures containing the test substances and semi-liquid vehicles are mechanically introduced into the chambers. Suitable semi-liquid vehicles are the customary basis used for creams, ointments of pastes. petroleum jelly sold under the trademark "VASELINE". is preferred but adeps lanae and oily cream are also quite suitable.

Examples of typical test allergens are mafenide, benzocaine, procaine hydrochloride, neomycin sulphate, Peru balsam, formalin, tetramethylthiuran disulphide, 2-mercaptobenzothiazole, chloroiodohydroxyquinoline, turpentine, potassium dichromate, nickel sulphate, cobalt sulphate, colophony, mercury(II) chloride, epoxy resins, p-phenylene-diamine, p-toluylenediamine, p-aminodiphenylamine hydrochloride, N-phenyl-N'-isopropyl-p-phenylenediamine, PHB esters (mixture of methyl, ethyl, propyl, isopropyl, butyl and benzyl p- hydroxybenzoates) and wood tars (mixtures of spruce, beech, juniper and birch wood tars).

The occlusion chambers in the customary "FINN CHAMBERS" have an internal diameter of about 6–10 mm, preferably about 8 mm., a depth of 0.3–1 mm, preferably about 0.5 mm and a volume of about 0.01–0.1 ml, preferably about 0.025 ml. The optimum volume introduced is about 0.005 to 0.05 ml, preferably about 0.01 to 0.02 ml, in particular about 0.012 to 0.015 ml.

It is preferable in the actual introduction process to project the requisite amount of substance into the chambers by the jet principle, using a compressed air valve, at temperatues between about 20° and 50° C. (depending on the substance).

The chosen temperature is preferably such that the product is liquified, but is only briefly (for a maximum of about 20 seconds) exposed to heat. Virtually no sedimentation takes place if this is the case, especially since the material to be introduced is exposed to large acceleration forces. Immediately after the mixture has been measured into the chambers it solidifies again, thus resulting in "ointment drops" in the form of segments of a sphere ranging from lenticular to hemispherical. The brief liquifaction means that it is possible to achieve the requisite accuracy of volume of the doses, which presents a great problem when measuring when cold. At the same time, this conservative procedure does not impair the allergic potency or the quality of the test substances.

Accurate adjustment of the volume of the dose and the desired shape of the "ointment drops" as a segment of a sphere is controlled by the block temperature of the valve, the pressure with which the mixture is delivered, the geometry of the delivery nozzle, and the time the valve is open.

The plasters are preferably made up into strips, each of which contains three to ten, preferably five, chambers containing test allergens.

To improve handling and storage and for satisfactory transport, the plaster, for example in the form of the strips which have been mentioned, is enveloped in a protective pack which preferably consists of an upper foil and a lower foil which enclose the actual test plaster in the manner of a sandwich. An example of a suitable foil material is aluminum which is coated with inert material, in particular with polypropylene which contains no plasticizer or stabilizer. The polypropylene layers are in mutual contact; hence the test plaster is hermetically protected from environmental effects.

It is possible and preferable for the upper foil additionally to have over each of the test chamber positions hemispherical stabilizing convexities which prevent contact with the test substance "drops", which are in the form of a segment of a sphere, and hence any adverse effect on the quantity of the substance which is located on the test plaster and has been accurately measured. A dimpled texture on the upper foil can preserve the adhesive surfaces on the sandwiched test plaster and reduce the pulloff forces necessary for tearing open the protective foil.

A particular embodiment of the plaster is shown in the drawings. Since the plaster is in the shape of an arrow, the upper and lower ends of the plaster strip and hence the positions of the test allergens in the aluminum chambers on the patient's back are clearly identified, so that no mistake is made between the upper and lower ends, and thereby presenting the vertical sequence of the individual test substances on inspection.

A further embodiment of the test plaster provides additionally a possibility to differentiate qualitatively and optically various test plaster strips located on the back of the patient from one another.

This additional optical marking is important when, i.e., the different test plasters are removed from the back of the patient after 24 to 48 hours and the respective skin reactions are read by the physician about 30 minutes later.

Referring now more specifically to the drawings, it is seen that a package for a plaster, designated generally by the numeral 10 is configured of a top foil 11, a plaster 12 and a bottom foil 13, laminated together, as is shown in FIGS. 1 and 3, to form the package. The plaster 12 is an elongated strip with a plurality of test sites, designated generally by the numeral 14 thereon. Each test site includes a circular aluminum plate 16 which is adhered to the plaster 12 and an ointment drop 17 which includes a semi-liquid vehicle suspending a test allergen therein. Each plate 16 includes a raised rim 19 which cooperates with a dome 20 on the top foil 11 to form an occlusion chamber as is seen in FIG. 3. In accordance with a preferred embodiment of the invention, each test site 14 is aligned with a dome 20 so that the linear array of test sites is protected by the top foil 11.

The plaster 12 is sandwiched between the top foil 11 and bottom foil 13 and the bottom foil 13 is bonded to the top foil 11 along an area 23 disposed outboard of the plaster 12. In accordance with an embodiment of the invention, the top foil 11 and bottom foil 13 are each made of aluminum and coated with an inert material such as polypropylene which contains no plasticizer or stabilizer. Along the area where the foils are in direct contact, i.e., the area outside the periphery of the plaster 12, the foils are bonded together and hermetically sealed so as to prevent air from contacting the moisture drops 17. The seal may be effected by conventional means so that the polypropylene coating the foils 11 and 13 adhere together. For example, the seal may be affected by pressure along the narrow width bonding area 23 or perhaps by a combination of heat and pressure or any of the conventional method of sealing strips of aluminum foil coated with polypropylene.

When one wishes to use the plaster strip 12, the package 10 is delaminated by separating the unbonded area 25 on the top foil 11 from the unbonded area 26 on the bottom foil 13 by pulling the two foils apart as is seen in FIG. 4. The foils separate along the narrow width bonding area 23. The plaster 12 is then separated from the top foil 11 by peeling it from the top foil. The plaster 12 has adhesive 27 on one surface thereof which adheres to a multiplicity of dimples 28 on the top foil so that it is relatively easy to pull the plaster from the top foil without tearing the plaster. The plaster has no adhesive on its other suface. Since the plates 16 carrying the ointment drops 17 are adhered to the adhesive surface 27 of the plaster 12, they remain on the plaster 12 as the plaster is peeled. The plaster 12 is then applied to the skin of the patient and adhered thereto by the adhesive surface 27.

According to the prior art approaches, in order to identify the respective (negative or positive) test reactions on the skin of the patient, usually the kind and the sequence of the substances of each test strip are noted directly on the back skin of the patient with a special skin marking crayon so that the exact assignment of the skin reactions to the tested substances is possible. This kind of skin marking for an unequivocal recognition and identification of the test reactions is very time-consuming and inconvenient for the patient because of possible discolorations. It is avoided by the arrangement of the instant invention.

A dividing line (or perforation) 33 set forth in the following discussion is placed proximate the upper edge of the plaster. The perforation 33 permits the lower part of the plaster strip containing the test sites 14 to be removed after the test time has expired, whereas the smaller section of the plaster above the dividing line (perforation 33) remains affixed to the back of the patient. This small plaster section can be marked with a code number or code letter by the manufacturer, which code number or letter indicates a defined sequence of certain test substances. For example, a test strip could be marked with Roman number I so as to designate and fix five test allergens in a defined sequence and test concentration. Specifically a standard sequence "I" could have the arrangement from above to below: potassium dichromate 0.5%, benzocaine 5%, tetramethylthiuram disulfide 1%, formaldehyde 1%, adeps lanae 30% (these are the first five test allergens of a sequence of the "West German Standard" containing the 20 most important contact allergens).

The new test plaster is straightforward to use. The user, for example the physician or the physician's assistant, merely needs to tear open the protective pack and to apply the plaster strips. There is no longer the hitherto customary time-consuming and troublesome introduction into the test chambers under the pressure of time, or the erratic introduced amounts and the inaccurate test results arising from this.

Use of the new test plaster makes it possible for results to be checked with greater accuracy and increased reliability with subsequent checks of the tests. Since the test allergens are always applied in constant quality, accurate dosage and, preferably, in an occlusion chamber which is lined with inert material, the risk of false-negative or false-positive reactions is reduced. Compared with customary practice, time is saved because troublesome manual introduction into the chambers in the allergy laboratory is no longer necessary. Finally, it is possible by use of the new test plaster to provide the practicing physician carrying out the tests with a large number of test allergens, including unusual ones. This is because the problems associated with the transport and storage of the test plasters have been eliminated by the protective pack described.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A plaster package utilized for skin patch tests comprising: a plaster which is ready for use for skin patch tests, the plaster having a plurality of occlusion chambers of aluminum lined with a thin film of inert plastic, each of the occlusion chambers containing a test allergen, each of which allergens is in a semiliquid vehicle with doses of defined volume, and means for enveloping the plaster and occlusion chambers in a protective pack said enveloping means being defined by a pair of opposed foils bonded together with a hermetic seal and containing the plaster and occlusion chambers therebetween.

2. A plaster package containing allergens for conducting skin patch tests on patients, the plaster package comprising:
   a plaster having a periphery, a first surface and second surface, the first surface having an adhesive thereon for adhering the plaster to the skin of the patient;
   a plurality of plates of aluminum lined with a thin film of inert plastic distributed over the first surface of the plaster in a fixed array;
   a semiliquid vehicle on each plate, each semiliquid vehicle containing a test allergen therein;
   a first foil, the first foil having a periphery extending beyond the periphery of the plaster and having an inner surface with a plurality of concavities distributed therein in an array corresponding to the array of plates on the plaster, wherein when the first foil is adhered to the first surface of the plaster, the array of concavities cooperate with the array of plates to form a plurality of occlusion chambers with the semiliquid vehicles therein;
   a second foil abutting the second surface of the plaster and overlying the first foil with the plaster sandwiched therebetween, the second foil having a periphery extending beyond that of the plaster; and
   means for adhering the second foil to the first foil outside of the periphery of the plaster.

3. The plaster package of claim 2, wherein the plaster has a perforated line there-across dividing the plaster in two portions, the first portion having the aluminum chambers therein and the second portion being free of the aluminum chambers; code indicia on the second portion identifying the array of doses on the first portion, whereby the first portion may be removed at the perforation and the second portion retained on the patient with identification as to the particular patch test conducted.

4. The plaster of claim 3, further including direction indicia in the form of an arrow.

5. The plaster of claim 2, further including direction indicia in the form of an arrow.

6. The plaster package of claim 1, wherein the semiliquid vehicle is selected from the group consisting of petroleum jelly, adeps lineal and oily cream.

7. The plaster package of claim 1, wherein the semiliquid vehicle is petroleum jelly.

8. The plaster package of claim 2, wherein the semiliquid vehicle is selected from the group consisting of petroleum jelly, adeps lineal and oily cream.

9. The plaster package of claim 2, wherein the semiliquid vehicle is petroleum jelly.

10. The plaster package of claim 1, wherein the semiliquid vehicle and test substance are the only substances contained in the occlusion chamber.

11. The plaster package of claim 2, wherein the semiliquid vehicle and test substance are the only substances contained in the occlusion chamber.

12. A method of preparing a plaster package containing allergens for use in conducting skin patch tests, the method comprising the steps of:
   providing a plaster with an array of spaced aluminum plates arranged in a line;
   suspending separate allergens in semiliquid vehicles to form doses of different antigens;
   depositing on each of the aluminum plates on the plaster one of the semiliquid vehicles containing a dose of allergens,
   providing the plaster with directional indicia, and perforating the plaster to divide the plaster into a first portion having the array of aluminum chambers containing doses therein and a second portion having indicia thereon identifying the particular array of doses on the first portion, overlying one surface of the plaster with a first foil to cover the doses on the plates, and overlying the other surface of the plaster with a second foil to sandwich the plaster between the first and second foils.

\* \* \* \* \*